(12) United States Patent
Waggoner et al.

(10) Patent No.: US 11,571,173 B2
(45) Date of Patent: Feb. 7, 2023

(54) PRESSURE REGULATOR FOR X-RAY APPARATUS

(71) Applicant: Thermo Kevex X-Ray Inc., Scotts Valley, CA (US)

(72) Inventors: Alexander D. Waggoner, Hillsboro, OR (US); William Ferneau English, Boulder Creek, CA (US)

(73) Assignee: Thermo Kevex X-Ray Inc., Scotts Valley, CA (US)

( * ) Notice: Subject to any disclaimer, the term of this patent is extended or adjusted under 35 U.S.C. 154(b) by 351 days.

(21) Appl. No.: 15/929,814

(22) Filed: May 22, 2020

(65) Prior Publication Data

US 2020/0367843 A1 Nov. 26, 2020

Related U.S. Application Data

(60) Provisional application No. 62/852,510, filed on May 24, 2019.

(51) Int. Cl.
*F15B 15/14* (2006.01)
*A61B 6/00* (2006.01)

(52) U.S. Cl.
CPC ........ *A61B 6/4488* (2013.01); *F15B 15/1452* (2013.01); *F15B 15/1485* (2013.01)

(58) Field of Classification Search
CPC ...... F15B 15/14; F15B 15/1452; F15B 15/26; F15B 2201/3156; F15B 2201/40; F15B 2201/31; F15B 2201/312; A61B 6/4488
See application file for complete search history.

(56) References Cited

U.S. PATENT DOCUMENTS

| | | | |
|---|---|---|---|
| 2,808,068 A | 10/1957 | Fred et al. | |
| 5,610,968 A * | 3/1997 | Deucher | A61B 6/035 378/2 |
| 6,053,192 A | 4/2000 | Ellzey | |
| 6,074,092 A | 6/2000 | Andrews | |
| 6,519,317 B2 | 2/2003 | Richardson et al. | |
| 7,001,070 B2 * | 2/2006 | Kendall | H05G 1/025 378/200 |
| 7,221,736 B2 | 5/2007 | Heidrich et al. | |
| 7,481,241 B2 | 1/2009 | Carpenter et al. | |
| 10,203,705 B1 | 2/2019 | Rowe | |
| 2018/0112681 A1* | 4/2018 | Kloft | F15B 1/24 |

FOREIGN PATENT DOCUMENTS

| | | | | |
|---|---|---|---|---|
| EP | 1403523 A2 * | 3/2004 | | F15B 1/021 |
| GB | 2176242 | * 12/1986 | | F15B 1/053 |

OTHER PUBLICATIONS

English Translation of EP1403523A2.*

* cited by examiner

*Primary Examiner* — Thomas E Lazo
*Assistant Examiner* — Daniel S Collins (57) ABSTRACT

A pressure regulator for an x-ray apparatus includes a piston housing having a recess formed therein and a piston seated in the recess. The piston is free to reciprocate, and define a variable volume chamber, within the recess. A circumferential groove is formed in an exterior surface of the piston, and a seal is seated in the circumferential groove. A manifold in the piston housing places the chamber in fluid communication with an exterior of the piston housing.

21 Claims, 6 Drawing Sheets

PRESSURE REGULATOR FOR X-RAY APPARATUS

CROSS-REFERENCE TO RELATED APPLICATIONS

The present application claims the priority benefit from U.S. Patent Application Ser. No. 62/852,510, filed May 24, 2019, which is hereby incorporated by reference herein in its entirety for all purposes.

FIELD

Aspects of this disclosure relate generally to a pressure regulator for an X-ray apparatus with, and more particularly, a pressure regulator for an X-ray apparatus including a piston in a housing recess.

BACKGROUND

An X-ray apparatus and its associated components may generate large amounts of heat, which heat needs to be removed in order to maintain proper operating conditions for the X-ray apparatus. A closed circuit of coolant, such as a high voltage dielectric fluid, may be distributed throughout the X-ray apparatus by way of a pump, and then may be cooled as it passes through a heat exchanger. Removal of heat from the liquid coolant in the heat exchanger serves to cool various components of the X-ray apparatus. The closed fluid circuit operates best in the absence of air in the circuit and, therefore, the circuit may be exposed to vacuum during the filling process. There can be large pressure differentials between the closed fluid circuit and its surrounding environment, which are caused by temperature and pressure changes. Large temperature and pressure changes can result from operation of the X-ray apparatus itself, or from shipment of the device at high altitude. A pressure regulator within the closed circuit of liquid coolant may be used to help maintain the pressure within the closed circuit within desired limits.

Prior art pressure regulators may include bladders that are constructed of materials with collapsible and expandable properties. The collapsible nature of a bladder may prevent fluid flow under vacuum conditions, leading to problems in removing air from the circuit, and the bladder itself may be susceptible to damage.

It would be desirable to provide a pressure regulating device for an X-ray apparatus that reduces or overcomes some or all of the difficulties inherent in prior known processes. Particular objects and advantages will be apparent to those skilled in the art, that is, those who are knowledgeable or experienced in this field of technology, in view of the following disclosure and detailed description of certain embodiments.

SUMMARY

In accordance with a first aspect, a pressure regulator for an x-ray apparatus may include a piston housing having a recess formed therein. A piston may be seated in the recess, with the piston being free to reciprocate and define a variable volume chamber within the recess. A circumferential groove is formed in an exterior surface of the piston, and a seal is seated in the circumferential groove, which may perform in both static and dynamic states. A manifold in the piston housing places the chamber in fluid communication with an exterior of the piston housing.

In accordance with another aspect, an X-ray apparatus may include a housing, an X-ray assembly secured to the housing, and electrical components positioned within the housing. A closed circuit of coolant fluid is configured to draw heat from the X-ray assembly and the electrical components. A heat exchanger is positioned in the housing and is in fluid communication with the closed circuit of coolant fluid. A pump is configured to circulate the coolant fluid throughout the closed circuit. A piston assembly is positioned in the housing and is in fluid communication with the closed circuit of coolant fluid. The piston assembly includes a piston housing having a recess formed therein and a piston seated in the recess. The piston is free to reciprocate, and defines a variable volume chamber, within the recess. A circumferential groove is formed in an exterior surface of the piston, and a seal is seated in the circumferential groove, which may perform in both static and dynamic states. A manifold in the piston housing places the chamber in fluid communication with an exterior of the piston housing.

In accordance with a further aspect, an X-ray apparatus may include a housing, an X-ray assembly secured to the housing, and electrical components positioned within the housing. A closed circuit of coolant fluid is configured to draw heat from the X-ray assembly and the electrical components. A heat exchanger is positioned in the housing and is in fluid communication with the closed circuit of coolant fluid. A pump is configured to circulate the coolant fluid throughout the closed circuit. A piston assembly is positioned in the housing and is in fluid communication with the closed circuit of coolant fluid. The piston assembly includes a piston housing having a recess formed therein, and a piston seated in the recess. The piston is free to reciprocate, and define a variable volume chamber, within the recess. A circumferential groove is formed in an exterior surface of the piston, and a seal is seated in the circumferential groove, which may perform in both static and dynamic states. A manifold in the piston housing places the chamber in fluid communication with an exterior of the piston housing. A pair of opposed housing apertures is formed in the piston housing proximate an open end of the chamber, and an aperture extends through the piston. A locking pin includes a shaft and a head. The shaft is removably inserted through the pair of opposed housing apertures and the piston aperture to temporarily fix the piston with respect to the piston housing, and the head is seated on an external surface of the housing.

These and additional features and advantages disclosed here will be further understood from the following detailed disclosure of certain embodiments, the drawings thereof, and from the claims.

BRIEF DESCRIPTION OF THE DRAWINGS

The foregoing and other features and advantages of the present embodiments will be more fully understood from the following detailed description of illustrative embodiments taken in conjunction with the accompanying drawings in which.

The figures referred to above are not drawn necessarily to scale, should be understood to provide a representation of particular embodiments, and are merely conceptual in nature and illustrative of the principles involved. Some features depicted in the drawings have been enlarged or distorted relative to others to facilitate explanation and understanding. The same reference numbers are used in the drawings for similar or identical components and features shown in various alternative embodiments. Pressure regulators for X-ray apparatuses as disclosed herein would have configurations and components determined, in part, by the intended application and environment in which they are used.

DETAILED DESCRIPTION OF EMBODIMENTS

Figure 1A:
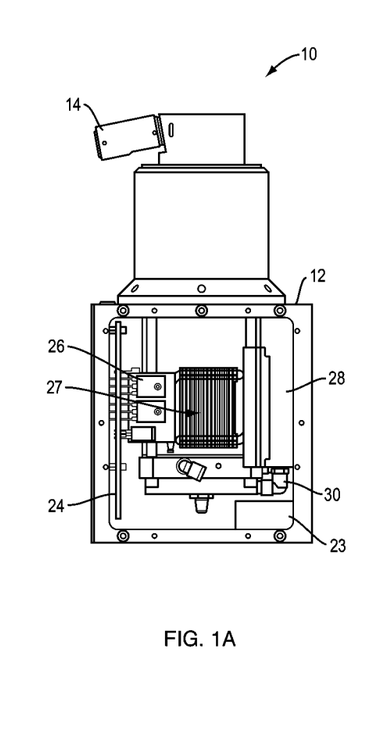
FIG. 1A-C are elevation views of an X-ray apparatus.
Figure 1B:
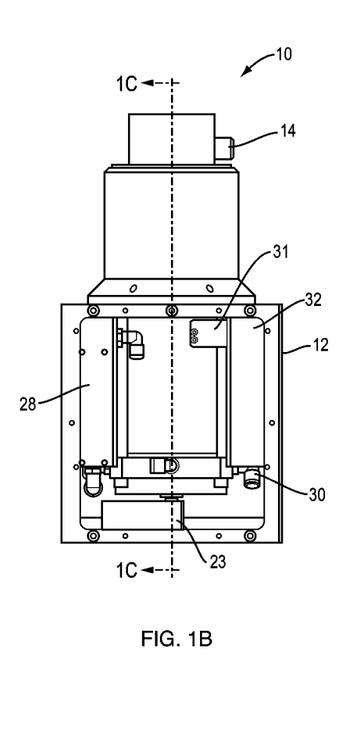
Figure 1C:
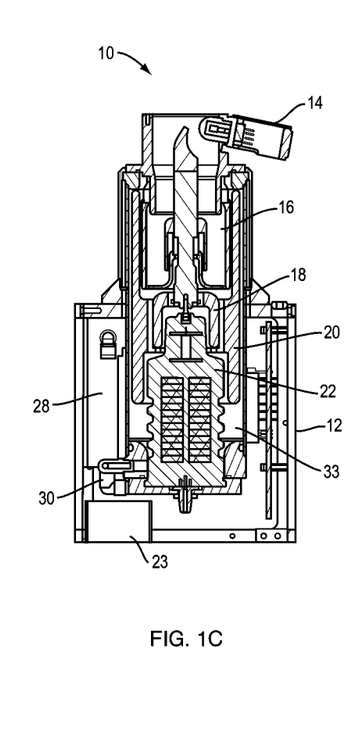

Referring to FIGS. 1A-C, an X-ray apparatus 10 is shown, which includes a housing 12. An X-ray source 14 with an electron gun cover is secured to an exterior of housing 12, with components of X-ray source 14 being positioned within housing 12, including a vacuum tube 16, a corona guard 18, a high voltage baffle 20, a high voltage multiplier 22 and a high voltage transformer 23. Also positioned within housing 12 are electrical components including a printed circuit board ("PCB") 24, heat dissipating electrical components 26, and a heat pipe assembly 27.

A heat exchanger 28 is connected to a closed circuit 30 of liquid coolant, which serves to remove heat from the components of X-ray apparatus 10. A pump 31 may be used to circulate the liquid coolant throughout closed circuit 30. Closed circuit 30 may comprise piping or other conduits to distribute the liquid coolant from pump 31 to heat exchanger 28 and to the other components within housing 12 in known fashion. Thus, closed circuit 30 may be configured to flow throughout housing 12 to remove heat from each of the components of X-ray apparatus 10. For example, as shown in FIG. 1C, closed circuit 30 includes a cavity 33 that surrounds high voltage multiplier 22 with liquid coolant in order to draw heat away from X-ray source 14. In certain embodiments, the liquid coolant is a high voltage dielectric fluid such as a transformer oil, including Diala® AX (available from Shell), for example. The liquid coolant may also be a perfluoropolyether ("PFPE") fluorinated fluid such as Galden® (available from Solvay), or Fluorinert™ (available from 3M™).

A pressure regulator 32 is in fluid communication with closed circuit 30, and serves to regulate the pressure of the liquid coolant in closed circuit 30. Pressure regulator 32 is configured to maintain an internal pressure of the closed circuit at or about the surrounding ambient pressure (e.g., one atmosphere when pressure regulator 32 is at sea level).

Figure 2:
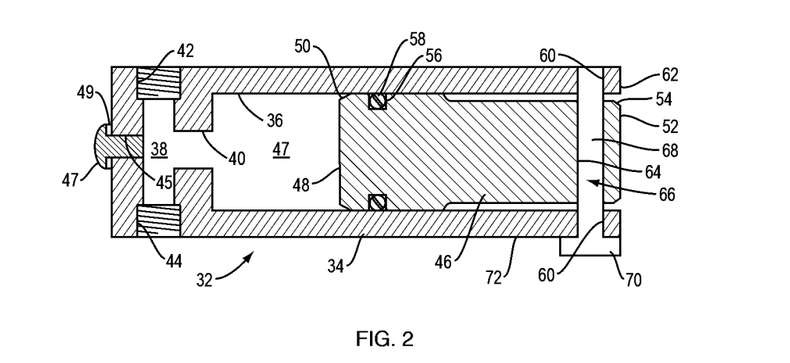
FIG. 2 is a section view of a pressure regulator of the X-ray apparatus of FIGS. 1A-C.
Figure 3:
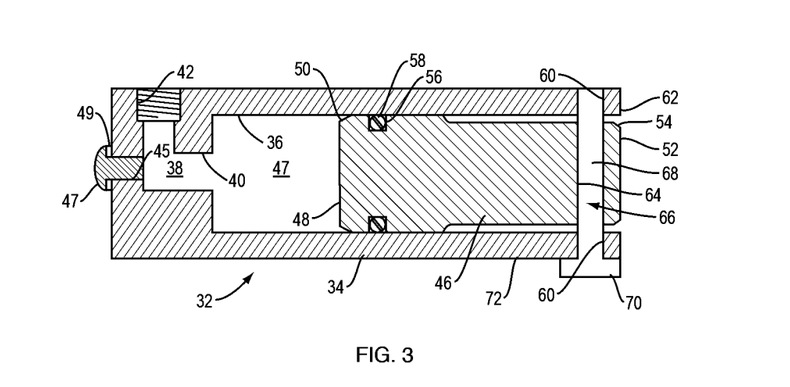
FIG. 3 is a section view of an alternative embodiment of a pressure regulator of the X-ray apparatus of FIGS. 1A-C.

As seen in FIG. 2, pressure regulator 32 includes a piston housing 34 having a recess 36 formed therein. A manifold 38 of piston housing 34 may place recess 36 in fluid communication with closed circuit 30. Manifold 38 may include a first port 40 open to recess 36. A second port 42 of manifold 38 may be connected to closed circuit 30 with a suitable connector or fitting. In the illustrated embodiment, second port 42 is threaded in order to threadingly engage a mating fitting (not shown) of closed circuit 30. A third port 44 of manifold 38 may be connected to closed circuit 30 with a suitable connector or fitting. In the illustrated embodiment, third port 44 is also threaded in order to threadingly engage a mating fitting (not shown) of closed circuit 30. In other embodiments, as illustrated in FIG. 3, manifold 38 of piston housing 12 may include only the first port 40 and second port 42, which serves as the sole fluid communication connection between recess 36 and closed circuit 30. Manifold 38 may include a fill port 45 that is used to fill closed circuit 30 with liquid coolant. After closed circuit 30 has been filled, fill port 45 may be sealed with a cap screw 47 and an O-ring 49.

A piston 46 may be seated in and reciprocate within recess 36, thereby defining a variable volume chamber 47 as the pressure within closed circuit 30 varies. Thus, variable volume chamber 47 is in fluid communication with closed circuit 30 by way of first port 40, second port 42, and third port 44 of manifold 38. In certain embodiments, piston 46 and recess 36 are circular. In the illustrated embodiment, an internal end 48 of piston 46 has a beveled edge 50, helping piston 46 move inwardly along recess 36. In certain embodiments, a portion of piston 46 proximate external end 52 of piston 46 may have a reduced diameter, or reduced thickness. External end 52 may also have a beveled edge 54 like beveled edge 50 at internal end 48.

A circumferential slot or groove 56 may be formed in the external surface of piston 46 proximate internal end 48. A seal 58 may be seated in groove 58. and serves to provide a hermetic seal between piston 46 and piston housing 34, helping maintain closed circuit 30 leak free, and reducing the chance of air entering the liquid coolant in closed circuit 30 during both static and dynamic states of closed circuit 30. Closed circuit 30 may be in a dynamic state during its operation, when piston 46 is free to move. Closed circuit 30 may be in a static state when it is being filled with liquid coolant, and piston 46 is fixed in place, as described in greater detail below.

Seal 58 may be an O-ring, for example. It is to be appreciated that seal 58 can take on any configuration and need not be an O-ring. Other suitable shapes and configurations for seal 58 will become readily apparent to those skilled in the art, given the benefit of this disclosure. In certain embodiments, seal 58 is formed of an elastomeric material such as a nitrile rubber, or a fluoroelastomer rubber such as Viton® (available from The Chemours Company). Other suitable materials that are compatible with the temperature ranges and dielectric fluids used as liquid coolant in closed circuit 30 will become readily apparent to those skilled in the art, given the benefit of this disclosure.

Piston housing 34 and piston 46 may be formed of a rigid material, such as metal, which serves to help maintain the internal pressure of closed circuit 30 within acceptable limits. For example, piston 46 may be formed of a corrosive resistant metal such as aluminum, an aluminum alloy, stainless steel, a nickel alloy, copper, or a chemically resistant machinable high temperature plastic such as polyetheretherketone ("PEEK").

A pair of opposed housing apertures 60 may be formed in piston housing 34 proximate an open end 62 of recess 36. A piston aperture 64 may be formed in piston 46 proximate its external end 52. A locking pin 66 may be removably received in housing apertures 60 and piston aperture 64 to temporarily fix piston 46 with respect to piston housing 34.

Locking pin 66 may include a shaft 68 and a head 70. Shaft 68 may be received in housing apertures 60 and piston aperture 64, and head 70 may be seated on an external surface 72 of piston housing 34 when locking pin 66 is fully inserted.

Temporarily fixing piston 46 with respect to piston housing 34 with locking pin 66 is useful when closed circuit 30 is filled with liquid coolant, allowing the volume of closed circuit 30 to be constant during the filling process. When closed circuit 30 is being filled, removing all air from within closed circuit 30 can improve performance of the liquid coolant, which provides electrical isolation for the high voltage components of X-ray source 14. In certain embodiments, a vacuum environment is provided for closed circuit 30 as it is being filled. It is to be appreciated that the temperature of the liquid coolant when closed circuit 30 is being filled will drive the equilibrium pressure of closed circuit 30. It is to be appreciated that having closed circuit 30 be leak free helps ensure that no air will be admitted into the liquid coolant in closed circuit 30. The seals and fittings within closed circuit must therefore be able to withstand the pressures encountered by closed circuit 30 during operation. The number of sealing elements, and the stiffness, resilience, and deflection of the materials used to form the seals all affect their ability to withstand the forces involved during operation.

As seen in FIG. 2, piston 46 is fixed in a neutral or steady-state position. The volume of chamber 47 when piston 46 is in the neutral position should be designed to be large enough to compensate for the expected thermal shrinkage of the liquid coolant in closed circuit 30. Similarly, the length of recess 36 should be designed to accommodate for the expected thermal expansion of the liquid coolant in closed circuit 30.

Once closed circuit 30 has been completely filled, locking pin 66 can be removed, and piston 46 may reciprocate within recess 36 of piston housing 34. Piston 46 may oscillate about the neutral position as the pressure within closed circuit 30 increases or decreases, thereby altering the volume of chamber 47 and minimizing the gauge pressure within closed circuit 30. When closed circuit 30 has been filled with oil at nominal room temperature, which may be between approximately 60° F. and approximately 75° F., piston 46 is subject to 1 ATM of pressure, and zero pressure delta with locking pin 66 inserted or removed. When the temperature of the liquid coolant in closed circuit 30 is reduced, the volume of the liquid coolant decreases, and when the temperature of the liquid coolant in closed circuit 30 is increased, the volume of the liquid coolant increases. The position of piston 46 within recess 36 changes relative to the displacement of the liquid coolant to maintain approximately 1 ATM of pressure on either side of seal 58.

Figure 4:
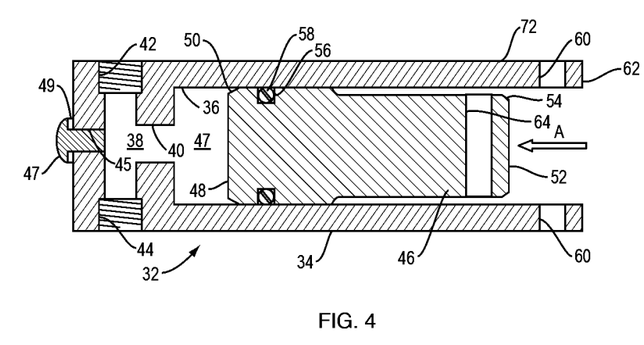
FIG. 4 is a section view of an alternative embodiment of the pressure regulator of FIG. 2, shown with the pressure regulator with a reduced oil volume.
Figure 5:
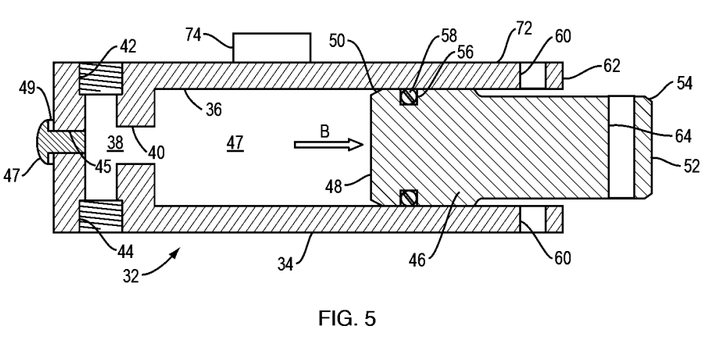
FIG. 5 is a section view of an alternative embodiment of the pressure regulator of FIG. 2, shown with the pressure regulator with an increased oil volume.

The operation of pressure regulator 32 is illustrated in FIGS. 4-5. As noted above, when locking pin 66 is removed from piston 46 and piston housing 34, piston 46 is free to move within recess 36, thereby varying the volume of chamber 36. As seen in FIG. 4, when the temperature of the liquid coolant is pressure within closed circuit 30 decreases, the volume of the liquid coolant decreases, with piston 46 forced inwardly into recess 36 in the direction of arrow A by the atmospheric pressure exerted on external end 52 of piston 46.

As seen in FIG. 5, when the temperature of the liquid coolant within closed circuit 30 increases, the volume of the liquid coolant increases, forcing piston 46 outwardly along recess 36 in the direction of arrow B. Piston 46 will continue to oscillate within recess 46 in the directions of arrows A and B, varying the volume of chamber 47 as the temperature of the liquid coolant within closed circuit 30 varies, thereby maintaining an internal pressure within closed circuit 30 at or near the surrounding ambient pressure of approximately 1 ATM.

Figure 6:
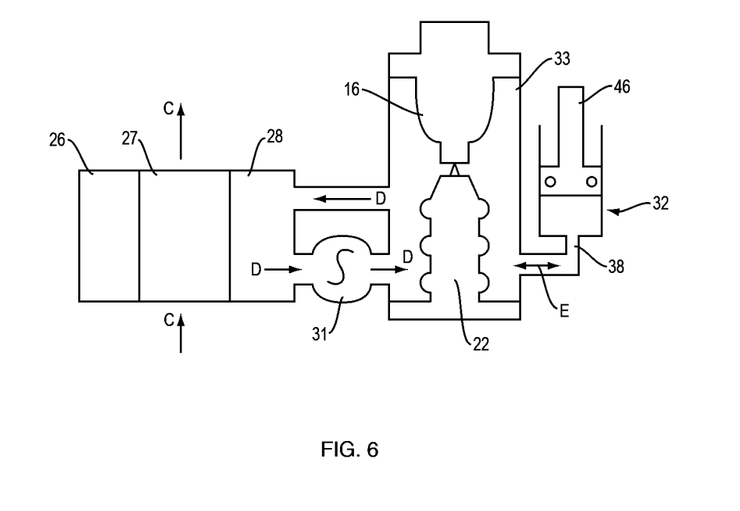
FIG. 6 is a schematic view of the components of the X-ray apparatus of FIGS. 1A-C shown connected to the pressure regulator of FIG. 2.

A schematic illustration of X-ray apparatus and its connection to pressure regulator 32 is shown in FIG. 6. As shown there, electrical components 26, such as power FETs, are coupled from a heatsink (not shown) to heat pipe assembly 27. As shown by arrows C air is drawn into and is blown out of heat pipe assembly 27 to assist with cooling. Heat exchanger 28, which draws heat from heat pipe assembly 27, cools that liquid coolant from closed circuit 30. Pump 31 distributes the liquid coolant in the direction of arrows C through oil cavity 33 in X-ray apparatus 10, thereby cooling HV multiplier 22 and vacuum tube 16. The liquid coolant then continues to flow through closed circuit 30 into heat exchanger 28 and then is returned to pump 31. Pressure regulator 32, which is connected to closed circuit 30 by way of manifold 38 serves to regulate pressure within closed circuit, as indicate by arrow D, which indicates oscillation of the flow of liquid coolant into and out of chamber 47 as the pressure within closed circuit 30 varies.

While the pressure within closed circuit 30 is controlled through the use of pressure regulator 32, it is to be appreciated that the temperature of various elements of X-ray apparatus 10 is monitored as well. For example, the temperature of PCB 24, the heatsink, and the housing for oil cavity 33 of closed circuit 30 may be monitored. Use of pressure regulator 32 in X-ray apparatus 10 allows for temperatures of the liquid coolant above, and below, room temperature to result in a continuous pressure on all of the hermetic seals of X-ray apparatus 10. This helps prevent leaking during the filling process. It is to be appreciated that it is more often easier to pull vacuum on a seal and fail due to air leaking past a seal than it is for oil or other fluids to expand with pressure and bleed past the same seal. In the present embodiment, pressure regulator 32 works with X-ray apparatus for temperatures ranging from approximately minus 20° C. to approximately 70° C. or more.

In certain embodiments, monitoring the position of piston 46 can be used as an alternative way to measure the temperature of the liquid coolant in closed circuit 30. By tracking the position of piston 46 and comparing various positions of piston 46 to temperatures measured in different elements of X-ray apparatus 10, a correlation between the position of piston 46 and the temperature of the liquid coolant can be developed. Since the liquid coolant can be considered incompressible at 1 atmosphere. For practical purposes the relative volume that the liquid coolant occupies at various temperatures is a function of the expansion or contraction of the liquid coolant at those various temperatures. For example, hydraulic oil compresses 0.5% at 1000 psi. If the system is calibrated when the piston is in its fixed position at room temperature after filling closed circuit 30, the position of piston 46 is viable as a reference for the temperature of the liquid coolant averaged out across the entirety of closed circuit 30. Additionally, if the circulation of the liquid coolant is optimal, the temperature gradient of liquid coolant throughout closed circuit 30 would be almost negligible.

Tracking the position of piston 46 can then help in monitoring the system, which can help in detecting potential problems, including, for example, leaks in closed circuit 30, problems with pump 31 or heat pipe assembly 27. Knowing when the temperature is reaching a temperature beyond the designed operating temperature can allow a user to perform a system shutdown in order to diagnose any problems and prevent failure of components of X-ray apparatus 10.

As illustrated in FIG. 5, a position monitoring device 74 may be used to track the position of piston 46. Position monitoring device 74 may be a laser, for example, or a coil-based motion sensor. It is to be appreciated that a coil-based motion sensor may use a metal target element on piston 46, in which case piston 46 could be formed of a high performance plastic material. Other suitable position monitoring devices will become readily apparent to those skilled in the art, given the benefit of this disclosure.

Figure 7:
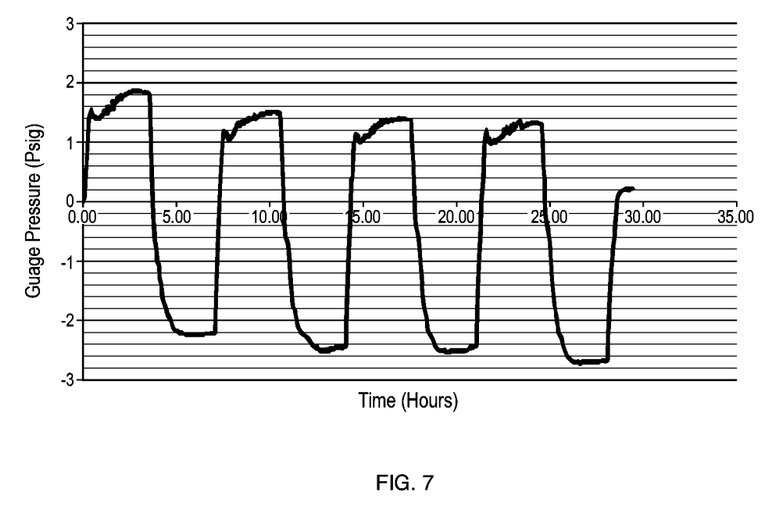
FIG. 7 is a graph showing an exemplary plot of gauge pressure over time for the pressure regulator of FIG. 2 as it is exposed to heat cycles.

An experiment was conducted to determine the effectiveness of pressure regulator 32 in maintaining the pressure within closed circuit 30 while X-ray apparatus 10 was exposed to a temperature cycling between approximately 0° C. and approximately 60° C. over a 30 hour period. As can be seen in the graph of FIG. 7, the gauge pressure within closed circuit varied between approximately 1.8 psig and approximately −2.75 psig. The positive pressures seen in FIG. 7 reflect higher pressure within closed circuit 30 and a movement of piston 46 in the direction of arrow B of FIG. 5. The negative pressures seen in FIG. 6 reflect lower pressure within closed circuit 30 and a movement of piston 46 in the direction of arrow A of FIG. 4.

Figure 8:
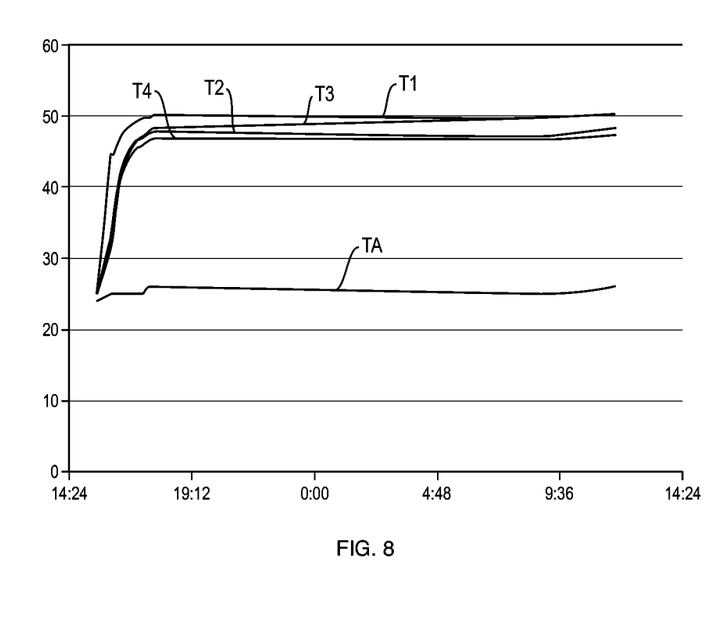
FIG. 8 is a graph showing an exemplary plot of temperature over time for the elements of the X-ray apparatus of FIGS. 1A-C.

FIG. 8 illustrates the temperature of various components of X-ray apparatus 10 over a 24 hour period of time with pressure regulator 32 maintaining the pressure within closed circuit 30. As seen here, with TA being the ambient temperature, the temperatures T1-T4 can be seen to stabilize after the first couple of hours of operation of the system and them remain stable throughout the remainder of the 24 hour period. In this embodiment, T1 is the temperature at the PCB 24, T2 is the temperature at heat exchanger 28, T3 is the temperature at the outer cone of X-ray apparatus 10 that surrounds vacuum tube 16, and T4 is the temperature at a lead cylinder around vacuum tube 16 within the outer cone of the X-ray apparatus 10. It can be seen here that after an initial ramping-up period, the temperature of the various components remained stable over the 24 hour period.

Those having skill in the art, with the knowledge gained from the present disclosure, will recognize that various changes can be made to the disclosed apparatuses and methods in attaining these and other advantages, without departing from the scope of the present invention. As such, it should be understood that the features described herein are susceptible to modification, alteration, changes, or substitution. For example, it is expressly intended that all combinations of those elements and/or steps which perform substantially the same function, in substantially the same way, to achieve the same results are within the scope of the invention. Substitutions of elements from one described embodiment to another are also fully intended and contemplated. The specific embodiments illustrated and described herein are for illustrative purposes only, and not limiting of the invention as set forth in the appended claims. Other embodiments will be evident to those of skill in the art. It should be understood that the foregoing description is provided for clarity only and is merely exemplary. The spirit and scope of the present invention are not limited to the above examples, but are encompassed by the following claims.

What is claimed is:

1. A pressure regulator for an x-ray apparatus comprising:
   a piston housing having a recess formed therein;
   a piston seated in the recess, the piston being free to reciprocate and define a variable volume chamber within the recess;
   a circumferential groove formed in an exterior surface of the piston;
   a seal seated in the circumferential groove;
   a manifold in the piston housing placing the chamber in fluid communication with an exterior of the piston housing;
   a pair of opposed housing apertures formed in the piston housing proximate an open end of the chamber;
   a piston aperture extending through the piston; and
   a locking pin removably received in the pair of opposed housing apertures and the piston aperture to temporarily fix the piston with respect to the piston housing.

2. The pressure regulator of claim 1, wherein the locking pin includes a shaft inserted through the pair of opposed housing apertures and the piston aperture, and a head seated on an external surface of the housing.

3. The pressure regulator of claim 1, wherein the manifold includes a first port opening into the chamber and a second port opening to an exterior of the housing.

4. The pressure regulator of claim 3, wherein the second port is threaded.

5. The pressure regulator of claim 3, further comprising a third port opening to an exterior of the housing.

6. The pressure regulator of claim 5, wherein the second and third ports are threaded.

7. The pressure regulator of claim 1, wherein the seal is an O-ring.

8. The pressure regulator of claim 1, wherein the seal is formed of an elastomeric material.

9. The pressure regulator of claim 1, wherein the piston housing and piston are formed of aluminum.

10. The pressure regulator of claim 1, wherein the piston housing and piston are formed of stainless steel.

11. An X-ray apparatus comprising:
    a housing;
    an X-ray assembly secured to the housing;
    electrical components positioned within the housing;
    a closed circuit of coolant fluid configured to draw heat from the X-ray assembly and the electrical components;
    a heat exchanger positioned in the housing and being in fluid communication with the closed circuit of coolant fluid;
    a pump configured to circulate the coolant fluid throughout the closed circuit; and
    a piston assembly positioned in the housing and being in fluid communication with the closed circuit of coolant fluid, the piston assembly comprising:
       a piston housing having a recess formed therein;
       a piston seated in the recess, the piston being free to reciprocate and define a variable volume chamber within the recess;
       a circumferential groove formed in an exterior surface of the piston;
       a seal seated in the circumferential groove;
       a manifold in the piston housing placing the chamber in fluid communication with an exterior of the piston housing;
       a pair of opposed housing apertures formed in the piston housing proximate an open end of the chamber;
       a piston aperture extending through the piston; and
          a locking pin removably inserted through the pair of opposed housing apertures and the piston aperture to temporarily fix the piston with respect to the piston housing.

12. The X-ray apparatus of claim 11, wherein the locking pin includes a shaft inserted through the pair of opposed housing apertures and the piston aperture, and a head seated on an external surface of the housing.

13. The X-ray apparatus of claim 11, wherein the manifold includes a first port opening into the chamber and a second port opening to an exterior of the housing.

14. The X-ray apparatus of claim 13, wherein the second port is threaded.

15. The X-ray apparatus of claim 13, further comprising a third port opening to an exterior of the housing.

16. The X-ray apparatus of claim 15, wherein the second and third ports are threaded.

17. The X-ray apparatus of claim 11, wherein the seal is an O-ring.

18. The X-ray apparatus of claim 11, wherein the seal is formed of an elastomeric material.

19. The X-ray apparatus of claim 11, wherein the piston housing and piston are formed of aluminum.

20. The X-ray apparatus of claim 11, wherein the piston housing and piston are formed of stainless steel.

21. An X-ray apparatus comprising:
a housing;
an X-ray assembly secured to the housing;
electrical components positioned within the housing;
a closed circuit of coolant fluid configured to draw heat from the X-ray assembly and the electrical components;
a heat exchanger positioned in the housing and being in fluid communication with the closed circuit of coolant fluid;
a pump configured to circulate the coolant fluid throughout the closed circuit;
a piston assembly positioned in the housing and being in fluid communication with the closed circuit of coolant fluid, the piston assembly comprising:
  a piston housing having a recess formed therein;
  a piston seated in the recess, the piston being free to reciprocate and define a variable volume chamber within the recess;
  a circumferential groove formed in an exterior surface of the piston;
  a seal seated in the circumferential groove; and
a manifold in the piston housing placing the chamber in fluid communication with an exterior of the piston housing;
a pair of opposed housing apertures formed in the piston housing proximate an open end of the chamber;
an aperture extending through the piston; and
a locking pin including a shaft removably inserted through the pair of opposed housing apertures and the piston aperture to temporarily fix the piston with respect to the piston housing, and a head seated on an external surface of the housing.

* * * * *